United States Patent [19]

Schildknecht et al.

[11] Patent Number: 4,996,198

[45] Date of Patent: Feb. 26, 1991

[54] ANTICOCCIDIAL COMPOSITION

[75] Inventors: Eugene G. Schildknecht, Hacketts Town; Govind G. Untawale, Wayne, both of N.J.

[73] Assignee: Hoffmann-La Roche Inc., Nutley, N.J.

[21] Appl. No.: 217,488

[22] Filed: Jul. 11, 1988

[51] Int. Cl.[5] ............... A61K 31/505; A61K 31/635; A61K 34/00

[52] U.S. Cl. .................................. 514/157; 424/115; 514/272

[58] Field of Search ................ 514/157, 272; 424/115

[56] References Cited

U.S. PATENT DOCUMENTS

| | | | |
|---|---|---|---|
| 3,461,206 | 8/1969 | Hoffer et al. | 514/157 |
| 3,715,372 | 2/1973 | Stempel et al. | 424/115 |
| 4,447,421 | 5/1984 | Klothen | 514/152 |

*Primary Examiner*—Allen J. Robinson
*Attorney, Agent, or Firm*—George M. Gould; Bernard S. Leon; Alan P. Kass

[57] ABSTRACT

Compositions comprising a mixture of a 2,4-diamino-5-(trisubstituted)benzyl-pyrimidine potentiated sulfonamide antibiotic with an ionophorous polyether anticoccidial agent are useful for the treatment and prevention of coccidiosis in animals.

4 Claims, No Drawings

ANTICOCCIDIAL COMPOSITION

BACKGROUND OF THE INVENTION

This invention relates to compositions useful for the prevention and treatment of coccidiosis in animals, methods of using the compositions and animal comestibles containing the compositions.

Coccidiosis is a troublesome disease which afflicts animals such as companion animals and ranch or farm animals raised commercially as a food source. The disease is caused by protozoal parasites called coccidia, which belong to the genus Eimeria. Typically, the infection occurs when the animal ingests food, water or fecal material contaminated with Eimeria organisms in the sporulated oocyst stage and the ingested oocysts enter the intestine and the cecum. The infection results in the destruction of the intestinal linings of the host animal, often leading to death. Even if the animals survive the infection, they grow more slowly than normal and the feed efficiency is adversely affected, causing significant economic losses if the infection involves large populations of food animals such as chickens, turkeys, geese, ducks, cattle, sheep and pigs.

Coccidiostatic agents are available for the prevention or treatment of coccidiosis. However, many of these agents are not entirely satisfactory in maintaining feed efficiency and weight gain, and others have very narrow safety and efficacy ranges and thus pose a risk to the animals being treated. Moreover, to a greater extent Eimeria organisms are developing resistance to the more frequently used coccidiostatic agents available on the market, thus limiting the effectiveness of such agents.

A widely used commercially available class of coccidiostats are those belonging to the group of polyether antibiotics isolated from various strains of bacteria. These substances are characterized by cyclic ether moieties in their chemical structures and are also commonly referred to as "ionophores" because of what is believed to be their transport-inducing mode of action. Among the more notable examples are lasalocid, monensin, salinomycin, lonomycin, narasin and maduramycin.

Non-ionophorous anticoccidial agents include those based on combinations of a sulfanilamide antibiotic and a potentiating 2,4-diamino-5-(2',4',5'-trisubstituted benzyl) pyrimidine. Combinations of this type are described in U.S. Pat. No. 3,461,206 (Hoffer and Mitrovic).

Potentiated sulfanilamides have experienced limited commercial use as anticoccidials due to their more moderate effectiveness compared to ionophores. Ionophorous anticoccidials, while possessing very good coccidiocidal activity as a class often pose difficulties in use because of their relatively narrow range of efficacy and the development of resistance to them.

SUMMARY OF THE INVENTION

The discovery has now been made that compositions containing a combination of (1) a potentiated sulfonamide and (2) an ionophore anticoccidial result in significantly enhanced activity against coccidiosis in animals caused by Eimeria organisms, especially ionophore-resistant strains. The anticoccidial activity of the present compositions against ionophore-resistant strains is greater than would be expected from a mere additive effect of the components.

Briefly, the present invention provides compositions containing the above mentioned active ingredients which are useful for the prevention and treatment of coccidiosis in animals. Additionally, the present invention includes a method for combating coccidiosis in animals, especially poultry, by orally administering the described compositions. Still further, this invention comprises animal comestibles and feed premixes containing the described compositions.

DETAILED DESCRIPTION OF THE INVENTION

The compositions of the present invention, when administered to animals such as companion animals (dogs, cats, etc.) and to animals raised commercially for food (poultry, cattle, sheep, pigs, etc.), are effective in the prophylaxis and treatment of coccidiosis. As has been discussed, the potentiated sulfonamide beneficially and synergistically interacts with the ionophorous component in the present compositions, resulting in greater activity against coccidiosis-causing strains of Eimeria. Because of their potentiated activity, these compositions are especially useful against virulent ionophore-resistant strains of Eimeria, including those comprising the coccidiosis-producing organisms which afflict poultry, such as E. tenella, E. maxima and E. acervulina. The present invention also makes possible the use of reduced amounts of the ionophorous component, thus lessening the risks normally associated with the utilization of many of these anticoccidial agents, such as toxicity and the concomitant effects on water intake, feeding pattern and nutrient absorption.

The sulfonamides are a known class of antibiotics which are characterized by the radical —$SO_2NH_2$. Suitable sulfonamides for these compositions are any of those that when combined with the described potentiator are useful in combating coccidiosis in animals, including the sulfonamides described in the previously mentioned U.S. Pat. No. 3,461,206.

Preferred for use in the practice of this invention are sulfadimethoxine, sulfamethoxazole, sulfadiazine and sulfadimethazine, especially sulfadimethoxine.

These sulfonamides are employed in the present compositions in conjunction with a potentiator of their activity, namely a substituted pyrimidine potentiator, and more specifically a 2,4-diamino-5-(trisubstituted)benzyl-pyrimidine sulfonamide potentiator of the formula

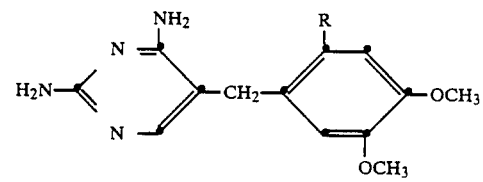

in which R is methoxy, methyl or ethyl.

Exemplary of suitable compounds within the above formula which are useful in the present compositions as potentiators for the sulfonamide are the following:

2,4-diamino-5-(2',4',5'-trimethoxybenzyl)pyrimidine (trimethoprim)

2,4-diamino-5-(2'-methyl-4',5'-dimethoxybenzyl)-pyrimidine (ormetoprim)

2,4-diamino-5-(2'-ethyl-4,5'-dimethoxybenzyl)pyrimidine

Especially preferred for use in the present compositions are combinations of sulfadimethoxine and ormetoprim.

The 2,4-diamino-5-(trisubstituted)benzyl-pyrimidine potentiator is generally employed in these compositions in amounts ranging from about 0.01 to about 20 parts by weights for each part by weight of the sulfonamide. More effectively, however, the weight ratio of the sulfonamide to the 2,4-diamino-5-(trisubstituted)benzyl-pyrimidine in the compositions is in the range from about 20:1 to about 1:1, with especially efficacious results being obtained using weight ratios of about 5:3 or about 5:1 (about 5:3 being the most favored).

As previously mentioned, the compositions of this invention also contain as an additional active ingredient the ionophore, which can be in the form of the antibiotic or its pharmaceutically acceptable salt or ester. The ionophore (polyether) component of these compositions can be any of the known anticoccidial ionophores such as, for example, lasalocid, monensin, maduramycin, narasin, nigericin, lonomycin, dianemycin and salinomycin, as well as the trimethylene glycyl ether of maduramycin. Still other ionophores useful as anticoccidials in the present compositions will occur to those skilled in the art from disclosure of such agents in the literature, for instance, Kirk-Othmer *Encyclopedia of Chemical Technology*, Vol. 3, 3rd Edition (1978).

The potentiated sulfonamide and the ionophore are employed in the compositions of this invention in relative proportions which are synergistic in combating coccidiosis-producing microorganisms, particularly against those strains that have developed resistance to individual ionophores.

The anticoccidial animal comestible compositions of this invention are prepared by mixing the active ingredients with a suitable carrier or diluent material which is generally used in animal feeds or drinking water. The concentration of the active ingredients in an animal comestible composition can be adjusted to meet particular needs and may be varied over a wide range. The minimum concentration should be such as to achieve the desired control of coccidiosis and the maximum concentration should be such as to avoid any undesired side effects when the comestible composition is ingested by the animal. Within these limitations, specific amounts will normally be regulated by the practitioner according to the potency and usual recommended dosing level for the individual active ingredients. A benefit from the potentiating interaction of the active ingredients is that the amount of each component required may be less then would ordinarily be necessary if they were used separately as a coccidiostat or anticoccidial. Thus, the amount of ionophore necessary may advantageously be reduced.

In preferred embodiments, medicated comestible compositions according to this invention will contain the potentiated sulfonamide component in concentrations from about 0.01 to about 0.02% by weight, with the concentration of the ionophore component being selected accordingly to achieve the desired degree of anticoccidial results.

To illustrate, an average recommended dosing level for lasalocid in poultry for the prevention of coccidiosis would be about 100 ppm (approved range 75–125 ppm). The compositions in accordance with this invention preferably contain the potentiated sulfonamide component and the ionophore component in proportions of from about 1.5 to about 2.5 parts by weight of the potentiated sulfonamide per part by weight of lasalocid, with resulting dosing levels of from about 75–125 to about 100–200 ppm of the lasalocid and potentiated sulfonamide, respectively, based on a typical dosing level for the ionophore.

Other preferred ionophore dose ranges for the present invention in combination with the potentiated sulfonamide dose levels of 100 to 200 ppm are as follows:

|  | Feed Dosage | |
|---|---|---|
| Monensin | 99–121 | ppm |
| Salinomycin | 44–66 | ppm |
| Narasin | 50–70 | ppm |
| Maduramycin | 5–7.5 | ppm |

In practice, the most convenient way to administer the active ingredients is to incorporate them by mixing into the animals' feed or drinking water. Any type of feed may be used, including common dry feeds, liquid feeds and pelleted feeds. The components can be added independently in the appropriate amounts necessary to achieve synergy, or they can be added in such amounts simultaneously as a mixture. Known methods of mixing may be utilized.

A preferred way for purposes of this invention is to prepare a concentrated additive premix of the active ingredients, which in turn can be added to the animals' feed to form a medicated comestible composition in accordance with this invention. The premix may be either in liquid or dry formulations. Separately formulated premixes for each of the active components can also be used to add them to a given feed lot to obtain the medicated comestible composition. In the usual case, premixes in accordance with this invention will contain from about 5 to about 200 grams of coccidiostat per pound of premix.

In formulating the animal comestible to contain the proper amounts of anticoccidial for treatment, one need only calculate the amount of the coccidiostat desired for administration to each animal, take into account the amount of feed per day normally consumed by the animal, compute the proper concentration of anticoccidial needed in the feed, and add the appropriate amount of anticoccidial or of premix to the feed to achieve that concentration.

The compositions of this invention are typically effective in combating coccidiosis when administered to animals in feed mixes containing the anticoccidial agent combination in an amount of from about 0.02 to about 0.04% by weight of the comestible (feed mix).

Other methods of administration may also be employed. For instance, the described anticoccidial agent can be incorporated into tablets, drenches, boluses or capsules and dosed to the animals. The preparation of such dosage forms can be accomplished using methods well known to those in the veterinary pharmaceutical art. These anticoccidial agents can also be administered by incorporation into the animals' drinking water.

The invention is further illustrated in the following examples.

EXAMPLE 1

Anticoccidial Activity of Sulfadimethoxine/Ormetoprim and Lasalocid Against *E. tenella*

Compositions in accordance with the present invention comprising sulfadimethoxine, ormetoprim (the weight ratio of these two ingredients was 5:3) and the ionophore lasalocid were evaluated against an *E. tenella* strain. The strain had been exposed in the field to commonly used coccidiostats, primarily ionophores over a long period of time with resulting reduced sensitivity to them as shown by higher mortality and average degrees of infection when tested against recommended dosing levels of such agents.

Two-week old broiler chickens, obtained from a commercial hatchery and kept in wire-floored, electrically heated battery brooders, were used in all studies. Ten birds, selected according to weight and sex (50% female and 50% male), were included in each group. The chickens were medicated two days before infection and maintained on the antibiotic until the termination of the trial, six days post-infection. UUC (uninfected, unmedicated controls) and IUC (infected, unmedicated controls) were also included in each study.

Broiler starter mash, a complete feed formula free of drugs, was used as the basal ration. The medicated feed was prepared by adding to the basal ration the desired concentration of drug or drugs. Each drug was thoroughly mixed into the mash prior to use to provide a uniform blend. In all instances, the medicated feed was fed two days before infection and for a total of eight consecutive days.

The infection was induced by giving to each bird 1.0 ml of a suspension containing 200,000 sporulated oocysts of E. tenella, properly agitated and suspended in sterile distilled water, which was inoculated directly into the crop by means of a blunt needle attached to a calibrated syringe.

At the termination of the trials, the surviving birds were sacrificed, necropsied, and scored for gross lesions. All birds that died during the experiments were also necropsied. Diagnosis was based on lesion location and morphology. The readings obtained were recorded as average degree of infection (ADI) according to the following scoring system: 0=normal, 1=slight, 2=moderate, 3=severe, 4=dead. The ADI was calculated based on the total of individual lesion scores divided by the number of birds scored.

In addition, weight gains (in % relative to UUC) and feed conversion (average feed consumption/average weight gain) were recorded.

The results for the E. tenella strain are shown below. In these Tables, "Feed Conv." stands for feed conversion and "Mort." stands for mortality. These results demonstrate that the combinations of sulfadimethoxine/ormetoprim and lasalocid have significantly greater activity than either sulfadimethoxine/ormetoprim or lasalocid alone, as reflected by the lower values for average degree of infection (ADI). Superior weight gains relative to the infected unmedicated control (IUC) are also shown. Lower lesion scores as reflected in ADI values will over longer periods of time translate into improved body weights and greater feed conversions.

| Treatment | Dosage (ppm) | Weight Gain, % | Feed Conv. | Mort. % | ADI |
| --- | --- | --- | --- | --- | --- |
| UUC | — | 100 | 1.65 | 0 | 0.0 |
| IUC | — | 70 | 2.06 | 12.5 | 3.1 |
| Sulfadimethoxine: Ormetoprim (5:3) | 200 | 91 | 1.77 | 0 | 1.2 |
| Lasalocid | 125 | 87 | 1.80 | 0 | 0.8 |
|  | 75 | 89 | 1.78 | 5 | 1.7 |
| Sulfadimethoxine: Ormetoprim (5:3) + Lasalocid | 200+ 125 | 80 | 1.98 | 0 | 0.0 |
|  | 200+ | 92 | 1.76 | 0 | 0.1 |
|  | 75 |  |  |  |  |

EXAMPLE 2

Anticoccidial Activity of Sulfadimethoxine/Ormetoorim and Monensin Against E. tenella The procedure described in Example 1 was repeated against a field strain of E. tenella which was ionophore-resistant as a result of exposure to monensin over a long period of time. The results show that 200+121 ppm and 200+99 ppm dose levels of the composition of sulfadimethoxine/ormetoprim (weight ratio 5:3) and monensin resulted in lower average degree levels of infection than the corresponding amounts of either sulfadimethoxine/ormetoprim or monensin used alone.

| Anticoccidial | Dosage (ppm) | Weight Gain, % | Feed Conv. | Mort. % | ADI |
| --- | --- | --- | --- | --- | --- |
| UUC | 0 | 100 | 1.74 | 0.0 | 0.0 |
| IUC | 0 | 78 | 2.33 | 20.0 | 2.9 |
| Sulfadimethoxine: Ormetoprim (5:3) | 200 | 89 | 1.93 | 5.0 | 1.6 |
| Monensin | 121 | 75 | 2.20 | 7.5 | 1.9 |
|  | 99 | 78 | 2.15 | 10.5 | 2.3 |
| Sulfadimethoxine: Ormetoprim (5:3) + Monensin | 200+ 121 | 74 | 2.24 | 2.5 | 1.3 |
| Sulfadimethoxine: Ormetoprim (5:3) + Monensin | 200+ 99 | 77 | 2.18 | 7.5 | 1.2 |

EXAMPLE 3

Anticoccidial Activity of Sulfadimethoxine/Ormetoprim and Salinomycin Against E. tenella The procedure described in Example 1 was repeated in an evaluation of anticoccidial activity against an ionophore-resistant field isolate of E. tenella, with inoculation again at 200,000 sporulated oocysts per bird, but using salinomycin as the ionophore. The results are give below:

| Anticoccidial | Dosage (ppm) | Weight Gain, % | Feed Conv. | Mort. % | ADI |
| --- | --- | --- | --- | --- | --- |
| UUC | 0 | 100 | 1.62 | 0.0 | 0.0 |
| IUC | 0 | 71 | 2.11 | 25.0 | 3.1 |
| Sulfadimethoxine: Ormetoprim (5:3) | 200 | 89 | 1.71 | 5.0 | 2.0 |
| Salinomycin | 60 | 81 | 2.01 | 5.0 | 2.1 |
| Sulfadimethoxine: Ormetoprim (5:3) + Salinomycin | 200+ 60 | 84 | 1.93 | 0.0 | 0.9 |

EXAMPLE 4

Anticoccidial Activity of Sulfadimethoxine/Ormetoprim and Narasin Against E. tenella The procedure of Example 1 was again repeated, using narasin as the ionophore, with the results shown below. Again, the combination with the ionophore was superior to either of the components used alone.

| Anticoccidial | Dosage (ppm) | Weight Gain, % | Feed Conv. | Mort. % | ADI |
|---|---|---|---|---|---|
| UUC | 0 | 100 | 1.66 | 0.0 | 0.0 |
| IUC | 0 | 51 | 2.63 | 17.5 | 3.1 |
| Sulfadimethoxine: Ormetoprim (5:3) | 200 | 71 | 2.12 | 5.0 | 2.0 |
| Narasin | 70 | 56 | 2.53 | 25.0 | 2.8 |
| Sulfadimethoxine: Ormetoprim (5:3) + Narasin | 200+ 70 | 76 | 1.91 | 2.5 | 1.6 |

EXAMPLE 5

Anticoccidial Activity of Sulfadimethoxine/Ormetoprim and Maduramycin Against *E. tenella*

Using the procedure of Example 1, an evaluation was made of the anticoccidial activity of sulfadimethoxine/ormetoprim (5:3) and the ionophore maduramycin against an ionophore-resistant isolate of an *E. tenella*. Once again, lower average degree levels of infection resulted from the use of the combination.

| Anticoccidial | Dosage (ppm) | Weight Gain, % | Feed Conv. | Mort. % | ADI |
|---|---|---|---|---|---|
| UUC | 0 | 100 | 1.69 | 0.0 | 0.0 |
| IUC | 0 | 48 | 2.68 | 30.0 | 3.2 |
| Sulfadimethoxine: Ormetoprim (5:3) | 200 | 72 | 2.17 | 0.0 | 1.8 |
| Maduramycin | 7 | 74 | 1.94 | 0.0 | 1.2 |
| Sulfadimethoxine: Ormetoprim (5:3) + Maduramycin | 200+ 7 | 83 | 1.87 | 0.0 | 0.3 |

EXAMPLE 6

Anticoccidial Activity of Sulfadimethoxine/Ormetoprim and Antibiotic X-14934A Against *E. tenella*

The procedure of Example 1 was repeated, using polyether antibiotic X-14934A as the ionophore (U.S. Pat. No. 4,510,317), with the results shown below.

| Anticoccidial | Dosage (ppm) | Weight Gain, % | Feed Conv. | Mort. % | ADI |
|---|---|---|---|---|---|
| UUC | 0 | 100 | 1.71 | 0.0 | 0.0 |
| IUC | 0 | 78 | 2.08 | 13.0 | 3.0 |
| Sulfadimethoxine: Ormetoprim (5:3) | 200 | 91 | 1.84 | 5.0 | 1.9 |
| Antibiotic X-14934A | 15 | 87 | 1.89 | 13.0 | 2.2 |
| Sulfadimethoxine: Ormetoprim (5:3) + Antibiotic X-14934A | 200+ 15 | 79 | 2.10 | 10.0 | 1.6 |

We claim:

1. A composition for combating coccidiosis in animals, which comprises sulfadimethoxine, ormetoprim and lasalocid, wherein these ingredients are present in amounts which in combination are synergistically effective in combating at least one coccidiosis-causing strain of Eimeria.

2. A comestible for feeding to animals, which comprises an animal feed containing an anticoccidial composition comprising sulfadimethoxine, ormetorpim and lasalocid, wherein the combination of sulfadimethoxine and ormetoprim is present in an amount from about 0.01 to about 0.02% by weight of the animal feed and the lasalocid is present in an amount which combined with the sulfadimethoxine and ormetoprim is synergistically effective in combating at least one coccidiosis-causing strain of Eimeria.

3. An animal feed additive premix containing an anticoccidial composition comprising sulfadimethoxine, ormetoprim and lasalocid, wherein the combination of sulfadimethoxine and ormetoprim is present in an amount from about 0.01 to 0.02% by weight of the animal feed and the lasalocid is present in an amount which combined with the sulfadimethoxine and ormetoprim is synergistically effective in combating at least one coccidiosis-causing strain of Eimeria.

4. A method of combating coccidiosis in animals, comprising orally administering to said animals a prophylactic or therapeutic amount of an anticoccidial composition comprising sulfadimethoxine, ormetoprim and lasalocid in amounts which in combination are synergistically effective in combating at least one coccidiosis-causing strain of Eimeria.

* * * * *